United States Patent
He et al.

(10) Patent No.: US 12,127,886 B2
(45) Date of Patent: Oct. 29, 2024

(54) METHOD, APPARATUS AND DEVICE FOR LOCATING REGION OF INTEREST OF TISSUE BASED ON ULTRASONIC DETECTION, AND STORAGE MEDIUM

(71) Applicant: WUXI HISKY MEDICAL TECHNOLOGIES CO., LTD., Jiangsu (CN)

(72) Inventors: Qiong He, Jiangsu (CN); Jinhua Shao, Jiangsu (CN); Jin Sun, Jiangsu (CN); Houli Duan, Jiangsu (CN)

(73) Assignee: WUXI HISKY MEDICAL TECHNOLOGIES CO., LTD., Jiangsu (CN)

( * ) Notice: Subject to any disclaimer, the term of this patent is extended or adjusted under 35 U.S.C. 154(b) by 284 days.

(21) Appl. No.: 17/631,111

(22) PCT Filed: Jul. 28, 2020

(86) PCT No.: PCT/CN2020/105023
§ 371 (c)(1),
(2) Date: Jan. 28, 2022

(87) PCT Pub. No.: WO2021/018109
PCT Pub. Date: Feb. 4, 2021

(65) Prior Publication Data
US 2022/0211349 A1 Jul. 7, 2022

(30) Foreign Application Priority Data
Aug. 1, 2019 (CN) .......................... 201910706603.6

(51) Int. Cl.
*A61B 8/00* (2006.01)
*A61B 8/08* (2006.01)

(52) U.S. Cl.
CPC ............ *A61B 8/469* (2013.01); *A61B 8/4245* (2013.01); *A61B 8/5269* (2013.01)

(58) Field of Classification Search
CPC ..... A61B 8/469; A61B 8/4245; A61B 8/5269; G01S 7/52046; G01S 7/52026; G01S 7/52077
See application file for complete search history.

(56) References Cited

U.S. PATENT DOCUMENTS

2010/0280383 A1* 11/2010 Kim .......................... G06T 7/11
600/453
2013/0303912 A1* 11/2013 Katsuyama .......... A61B 8/5207
600/447
(Continued)

FOREIGN PATENT DOCUMENTS

| CN | 102375992 A | 3/2012 |
|---|---|---|
| CN | 102481138 A | 5/2012 |

(Continued)

Primary Examiner — Joel Lamprecht
Assistant Examiner — Nyrobi Celestine
(74) Attorney, Agent, or Firm — SALIWANCHIK, LLOYD & EISENSCHENK

(57) ABSTRACT

Disclosed are a method, an apparatus and a device for locating a region of interest of a tissue, and a storage medium. The method comprising: acquiring ultrasonic echo signals from a detected region; identifying interfering regions and a region of interest in the detected region according to ultrasonic parameter values of the ultrasonic echo signals; judging whether the sizes of the interfering regions meet a preset condition or not; and if the sizes of the interfering regions meet the preset condition, removing interfering signals corresponding to the interfering regions from the ultrasonic echo signals. As such, the interfering signals may be removed while the interfering regions are small. Consequently, the region of interest can be adaptively located, and signals with interfering signals removed can be
(Continued)

used for signal processing and information extraction related to the region of interest, thereby increasing the accuracy and robustness of signal analysis related to the region of interest and improving the accuracy of a result of detection. (FIG. 1)

11 Claims, 3 Drawing Sheets

(56) References Cited

U.S. PATENT DOCUMENTS

| | | | | |
|---|---|---|---|---|
| 2014/0187947 | A1* | 7/2014 | Hansegard | A61B 8/469 |
| | | | | 600/443 |
| 2016/0157831 | A1* | 6/2016 | Kang | A61B 8/5276 |
| | | | | 600/443 |
| 2016/0242744 | A1* | 8/2016 | Mihailescu | G01S 7/52079 |
| 2016/0317130 | A1* | 11/2016 | Auvray | A61B 8/461 |
| 2019/0015075 | A1* | 1/2019 | Yoshiara | A61B 8/06 |
| 2019/0150889 | A1* | 5/2019 | Xu | A61B 8/5223 |
| 2019/0183462 | A1* | 6/2019 | Yang | G06F 18/2431 |
| 2019/0388057 | A1* | 12/2019 | Shen | A61B 8/4245 |
| 2020/0323514 | A1* | 10/2020 | Thienphrapa | A61B 8/4254 |

FOREIGN PATENT DOCUMENTS

| | | | |
|---|---|---|---|
| CN | 102961156 | A | 3/2013 |
| CN | 107331118 | A | 11/2017 |
| CN | 109965909 | A | 7/2019 |
| JP | 2001289942 | A | 10/2001 |

* cited by examiner

METHOD, APPARATUS AND DEVICE FOR LOCATING REGION OF INTEREST OF TISSUE BASED ON ULTRASONIC DETECTION, AND STORAGE MEDIUM

CROSS REFERENCE TO RELATED APPLICATIONS

This application is a National Stage of International Application No. PCT/CN2020/105023, filed on Jul. 28, 2020, which claims priority to Chinese Patent Application No. 201910706603.6, filed on Aug. 1, 2019; both of which are hereby incorporated by reference in their entireties.

TECHNICAL FIELD

The present invention relates to the technical field of ultrasonic detection, in particular to a method, apparatus and device for locating a region of interest of a tissue and a storage medium.

BACKGROUND

At present, when measuring the attenuation characteristic of a tissue, it is necessary to locate a region of interest of the tissue. Taking liver scanning as an example, the blood vessels, the bile duct and the kidneys and the intestinal duct near the liver in a liver image can interfere with signals. In the prior art, a region of interest cannot be adaptively located in real time, and a tissue image detected contains various interference information outside the region of interest, leading to a poor detection effect.

SUMMARY

The present invention provides a method, apparatus and device for locating a region of interest of a tissue and a storage medium, which are used for solving the problems that in the prior art, a region of interest cannot be adaptively located in real time, and a tissue image detected contains various interference information outside the region of interest, leading to an inaccurate result of detection of the region of interest.

One aspect of the present invention provides a method for locating a region of interest of a tissue, comprising:
  acquiring ultrasonic echo signals from a detected region by using an ultrasonic probe;
  identifying interfering regions and a region of interest in the detected region according to ultrasonic parameter values of the ultrasonic echo signals;
  judging whether the sizes of the interfering regions meet a preset condition or not; and
  if the sizes of the interfering regions meet the preset condition, removing interfering signals corresponding to the interfering regions from the ultrasonic echo signals.

Another aspect of the present invention provides an apparatus for locating a region of interest of a tissue, comprising:
  a measuring module, configured for acquiring ultrasonic echo signals from a detected region by using an ultrasonic probe;
  a region identification module, configured for identifying interfering regions and a region of interest in the detected region according to ultrasonic parameter values of the ultrasonic echo signals; and
  a location processing module, configured for:
  judging whether the sizes of the interfering regions meet a preset condition or not; and
  if the sizes of the interfering regions meet the preset condition, removing interfering signals corresponding to the interfering regions from the ultrasonic echo signals.

Another aspect of the present invention provides a device for locating a region of interest of a tissue, comprising:
  a memory, a processor, and a computer program stored in the memory and executable by the processor, wherein the processor implements the method for locating a region of interest of a tissue described above when running the computer program.

Another aspect of the present invention provides a computer-readable storage medium having a computer program stored therein, wherein
  the computer program implements the method for locating a region of interest of a tissue described above when executed by a processor.

According to the method, apparatus and device for locating a region of interest of a tissue and the storage medium provided by the present invention, ultrasonic echo signals from a detected region are acquired by using an ultrasonic probe; interfering regions and a region of interest in the detected region are identified according to ultrasonic parameter values of the ultrasonic echo signals; whether the sizes of the interfering regions meet a preset condition or not is judged; and if the sizes of the interfering regions meet the preset condition, interfering signals corresponding to the interfering regions are removed from the ultrasonic echo signals. As such, the interfering signals may be removed while the interfering regions are small. Consequently, the region of interest can be adaptively located, and signals with interfering signals removed can be used for signal processing and information extraction related to the region of interest, thereby increasing the accuracy and robustness of signal analysis related to the region of interest and improving the accuracy of a result of detection.

Figure 1:
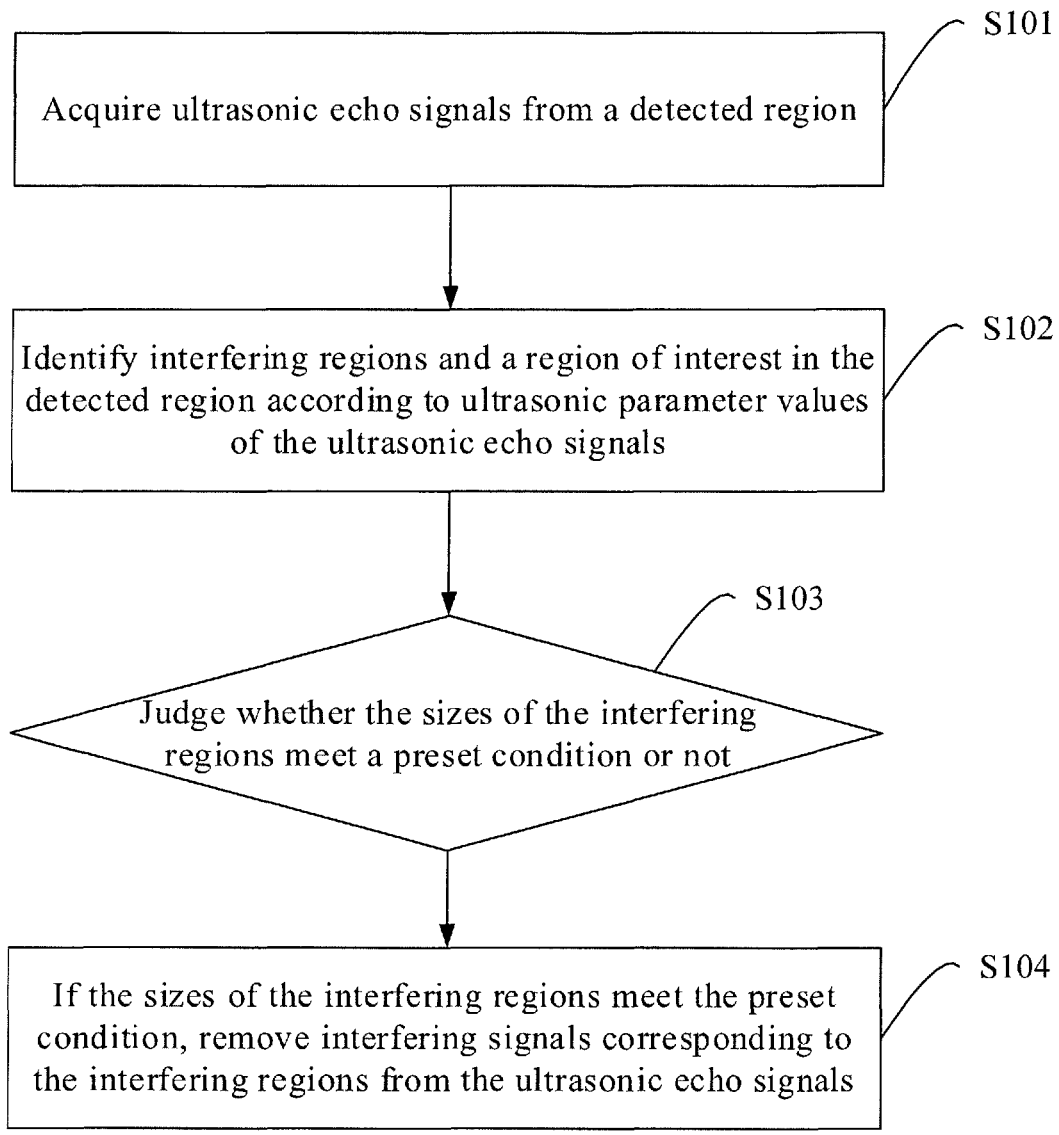
FIG. 1 is a flowchart of a method for locating a region of interest of a tissue according to Embodiment 1 of the present invention.

Through the above drawings, specific embodiments of the present invention have been shown, which will be described in more detail hereinafter. The drawings and written description are not intended to limit the scope of the inventive concept in any way, but rather to illustrate the inventive concept to those skilled in the art by reference to specific embodiments.

DETAILED DESCRIPTION

The exemplary embodiments will now be described in detail, and examples thereof are illustrated in the drawings. When reference to the drawings is made in the following description, identical numerals in the different drawings represent the same or similar elements, unless otherwise indicated. The implementations described in the following exemplary embodiments do not represent all implementations consistent with the present invention. Rather, they are merely examples of an apparatus and a method consistent with certain aspects of the present invention, as detailed in the appended claims.

The terms "first", "second", etc. referred to herein are used for descriptive purposes only and are not to be construed as indicating or implying relative importance or implicitly indicating the number of technical features indicated. In the description of the following embodiments, "a plurality of" means two or more, unless otherwise specifically defined.

These several specific embodiments below may be combined with one another, and the same or similar concepts or processes may not be repeated in some embodiments. The embodiments of the present invention will be described below with reference to the drawings.

Embodiment 1

FIG. 1 is a flowchart of a method for locating a region of interest of a tissue according to Embodiment 1 of the present invention. The embodiment of the present invention provides a method for locating a region of interest of a tissue, aiming at the problems that in the prior art, a region of interest cannot be adaptively located in real time, and a tissue image detected contains various interference information outside the region of interest, leading to an inaccurate result of detection of the region of interest.

As shown in FIG. 1, the method comprises the following specific steps:

S101: acquiring ultrasonic echo signals from a detected region;

An ultrasonic probe is used to emit detection waves to a tissue region of a detected object and receive ultrasonic echo signals generated by the detection waves passing through different tissues of the tissue region.

In this step, the ultrasonic echo signals from the detected region are acquired by using the ultrasonic probe.

S102: identifying interfering regions and a region of interest in the detected region according to ultrasonic parameter values of the ultrasonic echo signals;

The ultrasonic parameter at least includes, and may be one or more of, scattering peak, scatterer density, scatterer distribution characteristic, reflectance value and reflectance value distribution. In addition, the ultrasonic parameter may also be other parameters that can reflect different reflection or transmission characteristics of the different tissues to the detection waves, which is not specifically limited by this embodiment here.

In this embodiment, the region of interest may be any tissue region of a human body which can be detected adopting an ultrasonic detection method. The interfering regions may include interfering regions corresponding to one or more tissues. The region of interest and the interfering regions may vary when applied to different scenarios.

For example, taking liver scanning as an example, the region of interest may be a liver region, and the interfering regions may include the blood vessels and the bile duct near the liver, the kidneys, the intestinal duct and other tissues and organs near the liver, an acoustic shadow interfering region of the ribs, a gas interfering region of the lungs or the intestinal duct, and the like.

In addition, when the region of interest is the thyroid gland, the interfering regions may be the blood vessels, the trachea, the esophagus, a muscle tissue, and the like; when the region of interest is the mammary gland, the interfering regions may be muscle, an adipose tissue, and the like; when the region of interest is the spleen, the interfering regions may be the lungs, the ribs, the intestinal duct, the blood vessels, and the like; and when the region of interest is a specific muscle tissue or muscle group, the interfering regions may be muscles at other surrounding positions, a nearby adipose tissue, a nearby bone, and the like.

When applied to different scenarios, the region of interest and the interfering regions may vary, and this embodiment does not specifically limit the region of interest and the interfering regions corresponding to the region of interest.

Because the tissues have different reflection or transmission characteristics to the detection waves, the ultrasonic echo signals meeting characteristic parameter thresholds of the various tissues can be separated according to ultrasonic parameter values of the ultrasonic echo signals of the detection waves, so as to determine a region of interest or interfering regions corresponding to each tissue.

For example, when a reflection amplitude of ultrasonic echo signals in a certain region exceeds a threshold C and amplitudes of the upper and lower signals are uniform, for example, the ratio of a standard deviation to a mean of reflection amplitude changes of local regions of upper and lower boundaries in the region is less than a preset ratio (for example, the preset ratio may be 200%), the signals are considered as blood vessel signals; when a reflection amplitude of ultrasonic echo signals in a certain region is less than a threshold D, it is considered that there exists acoustic shadow interference from the ribs; or when scattering characteristics of a tissue reflect that signals have a characteristic of signals reflected by the gas of the lung or intestinal duct multiple times, it is considered that there exists interference from the lungs or intestinal duct. The threshold C may be set by a skilled person according to reflection characteristics of blood vessels to detection waves or experience and the threshold D may be set by the skilled person according to reflection characteristics of the ribs to detection waves or experience, which are not specifically limited by this embodiment here.

S103: judging whether the sizes of the interfering regions meet a preset condition or not;

After the interfering regions and the region of interest in the detected region are determined, the size of each interfering region in the detected region in an ultrasonic image can be calculated.

In this embodiment, the preset condition is used to judge whether interfering signals corresponding to the interfering regions can be directly removed. The preset condition may be whether a ratio of interfering regions to a target region is less than an interference ratio threshold, whether a ratio of interfering regions to a detected region is less than a total ratio threshold, whether the area of interfering regions is less than an interfering area threshold, or the like.

The interference ratio threshold, the total ratio threshold and the interfering area threshold may be set by the skilled person according to an actual application scenario and experience, which is not specifically limited by this embodiment here. For example, the value range of the interference ratio threshold may be [5%, 20%].

In addition, the preset condition may be set by the skilled person according to an actual application scenario and experience, which is not specifically limited by this embodiment here.

S104: if the sizes of the interfering regions meet the preset condition, removing interfering signals corresponding to the interfering regions from the ultrasonic echo signals.

When the sizes of the interfering regions meet the preset condition, that is, the interfering regions are small, and the removal of the interfering signals still cannot affect final signal processing for the region of interest, the interfering signals can be removed according to the positions of the interfering regions detected, and signals with interfering signals removed can be used for subsequent signal processing and information extraction related to the region of interest, thereby increasing the accuracy and robustness of signal analysis related to the region of interest and improving the accuracy of a result of detection.

Optionally, when the sizes of the interfering regions meet the preset condition, that is, the interfering regions are small, during calculation, the signals from the interfering regions can be directly removed from the ultrasonic echo signals, and will not be involved in subsequent calculation processing.

Optionally, when the sizes of the interfering regions meet the preset condition, that is, the interfering regions are small, during calculation, after the signals from the interfering regions are removed from the ultrasonic echo signals, the signals from the interfering regions can also be recovered into uniform signals by an interpolation method according to the signals from the other regions other than the interfering regions before subsequent calculation processing is performed.

The method for recovering the signals from the specified regions through the signals around the specified regions by adopting the interpolation method may be implemented by adopting any similar method in the prior art, which will not be repeated by this embodiment here.

In another implementation of this embodiment, when the sizes of the interfering regions meet the preset condition, that is, the interfering regions are small, the signals from the interfering regions may also be directly ignored.

According to the embodiment, ultrasonic echo signals from a detected region are acquired by using an ultrasonic probe; interfering regions and a region of interest in the detected region are identified according to ultrasonic parameter values of the ultrasonic echo signals; whether the sizes of the interfering regions meet a preset condition or not is judged; and if the sizes of the interfering regions meet the preset condition, interfering signals corresponding to the interfering regions are removed from the ultrasonic echo signals. As such, the interfering signals may be removed while the interfering regions are small. Consequently, the region of interest can be adaptively located, and signals with interfering signals removed can be used for signal processing and information extraction related to the region of interest, thereby increasing the accuracy and robustness of signal analysis related to the region of interest and improving the accuracy of a result of detection.

Embodiment 2

Figure 2:
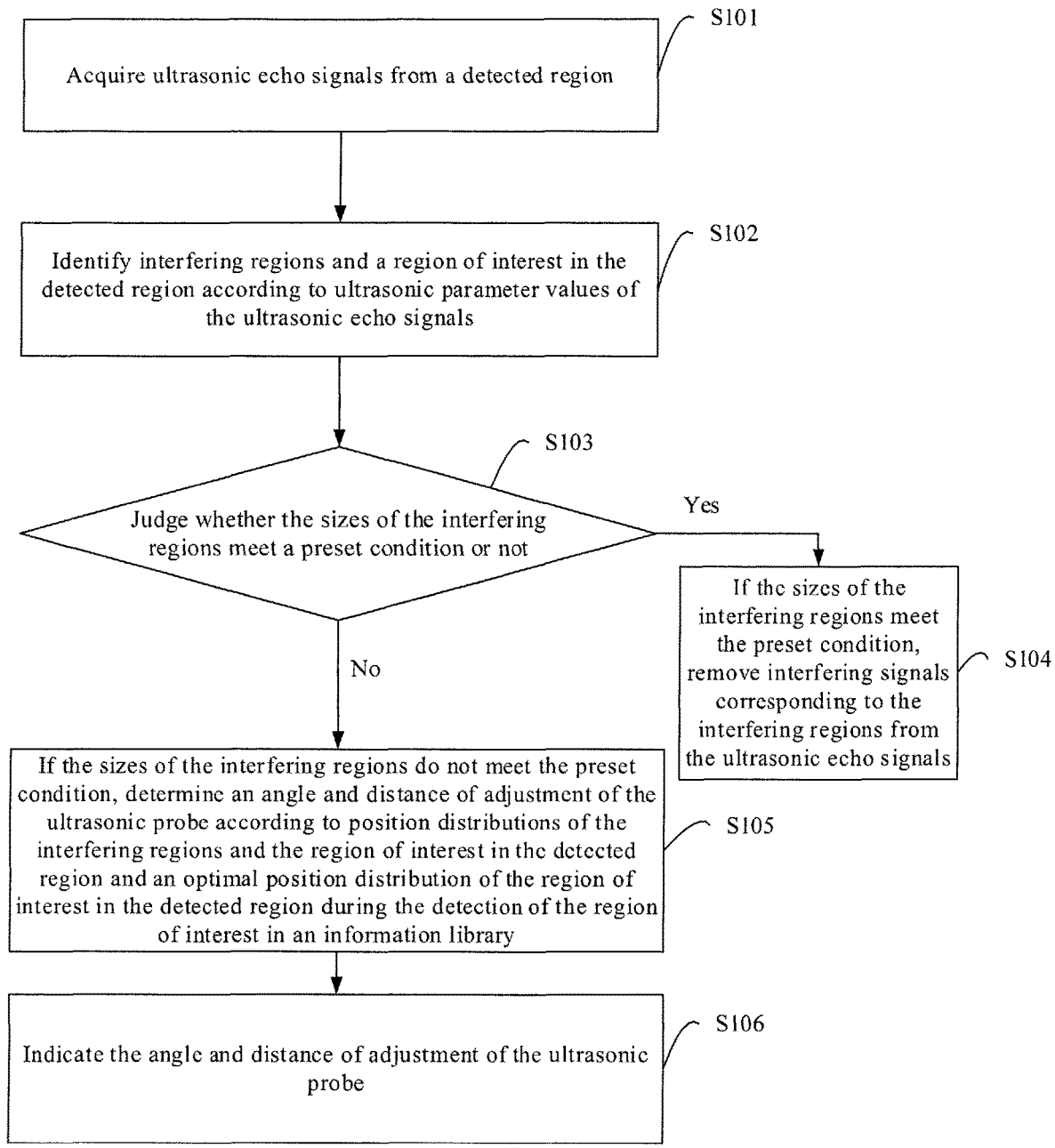
FIG. 2 is a flowchart of a method for locating a region of interest of a tissue according to Embodiment 2 of the present invention.

FIG. 2 is a flowchart of a method for locating a region of interest of a tissue according to Embodiment 2 of the present invention. On the basis of Embodiment 1 described above, in this embodiment, if the sizes of the interfering regions do not meet the preset condition, the ultrasonic probe is instructed to adjust its position to acquire ultrasonic echo signals from an updated detected region, and judgment processing is performed. As shown in FIG. 2, the method comprises the following specific steps:

S101: acquiring ultrasonic echo signals from a detected region;

An ultrasonic probe is used to emit detection waves to a tissue region of a detected object and receive ultrasonic echo signals generated by the detection waves passing through different tissues of the tissue region.

In this step, the ultrasonic echo signals from the detected region are acquired by using the ultrasonic probe.

S102: identifying interfering regions and a region of interest in the detected region according to ultrasonic parameter values of the ultrasonic echo signals;

The ultrasonic parameter includes, and may be, one or more of: scattering peak, scatterer density, scatterer distribution characteristic, reflectance value and reflectance value distribution. In addition, the ultrasonic parameter may also be other parameters that can reflect different reflection or transmission characteristics of the different tissues to the detection waves, which is not specifically limited by this embodiment here.

In this embodiment, the region of interest may be any tissue region of a human body which can be detected adopting an ultrasonic detection method. The interfering regions may include interfering regions corresponding to one or more tissues. The region of interest and the interfering regions may vary when applied to different scenarios.

For example, taking liver scanning as an example, the region of interest may be a liver region, and the interfering regions may include the blood vessels and the bile duct near the liver, the kidneys, the intestinal duct and other tissues and organs near the liver, an acoustic shadow interfering region of the ribs, a gas interfering region of the lungs or the intestinal duct, and the like.

In addition, when the region of interest is the thyroid gland, the interfering regions may be the blood vessels, the trachea, the esophagus, a muscle tissue, and the like; when the region of interest is the mammary gland, the interfering regions may be muscle, an adipose tissue, and the like; when the region of interest is the spleen, the interfering regions may be the lungs, the ribs, the intestinal duct, the blood vessels, and the like; and when the region of interest is a specific muscle tissue or muscle group, the interfering regions may be muscles at other surrounding positions, a nearby adipose tissue, a nearby bone, and the like.

When applied to different scenarios, the region of interest and the interfering regions may vary, and this embodiment does not specifically limit the region of interest and the interfering regions corresponding to the region of interest.

Because the tissues have different reflection or transmission characteristics to the detection waves, the ultrasonic echo signals meeting characteristic parameter thresholds of the various tissues can be separated according to ultrasonic parameter values of the ultrasonic echo signals of the detection waves, so as to determine a region of interest or interfering regions corresponding to each tissue.

Specifically, in this step, interfering regions and a region of interest in the detected region are identified according to ultrasonic parameter values of the ultrasonic echo signals and characteristic parameter thresholds of the tissue of interest and the interfering tissues.

The characteristic parameter threshold of each tissue is used to indicate the reflection or transmission characteristics of the tissue, and may be set by the skilled person according to a large number of experimental results and experiences, which is not specifically limited by this embodiment here.

For example, when a reflection amplitude of ultrasonic echo signals in a certain region exceeds a threshold C and amplitudes of the upper and lower signals are uniform, for example, the ratio of a standard deviation to a mean of reflection amplitude changes of local regions of upper and lower boundaries in the region is less than a preset ratio (for example, the preset ratio may be 200%), the signals are considered as blood vessel signals; when a reflection amplitude of ultrasonic echo signals in a certain region is less than a threshold D, it is considered that there exists acoustic shadow interference from the ribs; or when scattering characteristics of a tissue reflect that signals have a characteristic of signals reflected by the gas of the lung or intestinal duct multiple times, it is considered that there exists interference from the lung or intestinal duct. The threshold C may be set by a skilled person according to reflection characteristics of blood vessels to detection waves or experience and the threshold D may be set by the skilled person according to reflection characteristics of the ribs to detection waves or experience, which are not specifically limited by this embodiment here.

S103: judging whether the sizes of the interfering regions meet a preset condition or not;

After the interfering regions and the region of interest in the detected region are determined, the size of each interfering region in the detected region in an ultrasonic image can be calculated.

In this embodiment, the preset condition is used to judge whether interfering signals corresponding to the interfering regions can be directly removed. The preset condition may be whether a ratio of interfering regions to a target region is less than an interference ratio threshold, whether a ratio of interfering regions to a detected region is less than a total ratio threshold, whether the area of interfering regions is less than an interfering area threshold, or the like.

Specifically, a feasible implementation for judging whether the sizes of the interfering regions meet the preset condition or not is as follows:

judging whether the ratio of the interfering regions to the region of interest is less than an interference ratio threshold or not; if the ratio of the interfering regions to the region of interest is less than the interference ratio threshold, determining that the sizes of the interfering regions meet the preset condition; or if the ratio of the interfering regions to the region of interest is greater than or equal to the interference ratio threshold, determining that the sizes of the interfering regions do not meet the preset condition.

The interference ratio threshold may be set by the skilled person according to an actual application scenario and experience, which is not specifically limited by this embodiment here. For example, the value range of the interference ratio threshold may be [5%, 20%].

Optionally, another feasible implementation for judging whether the sizes of the interfering regions meet the preset condition or not is as follows:

judging whether the area of the interfering regions is less than an interfering area threshold or not; if the area occupied by the interfering regions in the detected region is less than the interfering area threshold, determining that the sizes of the interfering regions meet the preset condition; or if the area occupied by the interfering regions in the detected region is greater than or equal to the interfering area threshold, determining that the sizes of the interfering regions do not meet the preset condition.

The interfering area threshold may be set by the skilled person according to an actual application scenario and experience, which is not specifically limited by this embodiment here.

Optionally, another feasible implementation for judging whether the sizes of the interfering regions meet the preset condition or not is as follows:

judging whether the ratio of the interfering regions to the detected region is less than a total ratio threshold or not; if the ratio of the interfering regions to the detected region is less than the total ratio threshold, determining that the sizes of the interfering regions meet the preset condition; and if the ratio of the interfering regions to the detected region is greater than or equal to the total ratio threshold, determining that the sizes of the interfering regions do not meet the preset condition.

The total ratio threshold may be set by the skilled person according to an actual application scenario and experience, which is not specifically limited by this embodiment here.

In addition, the preset condition may be set by the skilled person according to an actual application scenario and experience, which is not specifically limited by this embodiment here.

In this step, if a result of judgment is that the sizes of the interfering regions meet the preset condition, it indicates that the interfering regions are small enough, and S104 is executed to directly remove the interfering signals corresponding to the interfering regions.

In this step, if a result of judgment is that the sizes of the interfering regions do not meet the preset condition, it indicates that the interfering regions are large, S105 and S106 are executed to automatically adjust the position of the ultrasonic probe, S101 is then executed to acquire ultrasonic echo signals from a new detected region by using the ultrasonic probe, and the region of interest of the tissue is relocated.

S104: if the sizes of the interfering regions meet the preset condition, removing interfering signals corresponding to the interfering regions from the ultrasonic echo signals.

When the sizes of the interfering regions meet the preset condition, that is, the interfering regions are small, and the removal of the interfering signals still cannot affect final signal processing for the region of interest, the interfering signals can be removed according to the positions of the interfering regions detected, and signals with interfering signals removed can be used for subsequent signal processing and information extraction related to the region of interest, thereby increasing the accuracy and robustness of signal analysis related to the region of interest and improving the accuracy of a result of detection.

Optionally, when the sizes of the interfering regions meet the preset condition, that is, the interfering regions are small, during calculation, the signals from the interfering regions can be directly removed from the ultrasonic echo signals, and will not be involved in subsequent calculation processing.

Optionally, when the sizes of the interfering regions meet the preset condition, that is, the interfering regions are small, during calculation, after the signals from the interfering regions are removed from the ultrasonic echo signals, the signals from the interfering regions can also be recovered into uniform signals by an interpolation method according to the signals from the other regions other than the interfering regions before subsequent calculation processing is performed.

The method for recovering the signals from the specified regions through the signals around the specified regions by adopting the interpolation method may be implemented by adopting any similar method in the prior art, which will not be repeated by this embodiment here.

In another implementation of this embodiment, when the sizes of the interfering regions meet the preset condition, that is, the interfering regions are small, the signals from the interfering regions may also be directly ignored.

S105: if the sizes of the interfering regions do not meet the preset condition, determining an angle and distance of adjustment of the ultrasonic probe according to position distributions of the interfering regions and the region of interest in the detected region and an optimal position distribution of the region of interest in the detected region during the detection of the region of interest in an information library.

If the sizes of the interfering regions do not meet the preset condition, it indicates that the interfering regions are large, and the removal of the interfering signals corresponding to the interfering regions will greatly affect a result of detection of the region of interest. In this embodiment, the position of the ultrasonic probe is adaptively adjusted through S105 and S106.

In this embodiment, ultrasonic echo signals which are obtained when ultrasonic detection is performed on each tissue region from a plurality of different angles and positions are stored in the information library in advance.

In this step, according to a preset model, the ultrasonic echo signals from the detected region are compared with the ultrasonic echo signals stored in the information library, so that an optimal position distribution of the region of interest in the detected region during the detection of the region of interest in the information library and angles and distances of deviation of position distributions of the interfering regions and the region of interest in the current detected region can be determined. Thus, an angle and distance of deviation of the current position of the ultrasonic probe relative to an optimal probe position can be determined, and an angle and distance of adjustment of the ultrasonic probe can be further determined.

S106: indicating the angle and distance of adjustment of the ultrasonic probe.

After being determined, the angle and distance of adjustment of the ultrasonic probe are indicated.

Exemplarily, after the angle and distance of adjustment of the ultrasonic probe are indicated, the position of the ultrasonic probe can be automatically controlled and adjusted according to the indicated information. Specifically, a control instruction which includes an angle and distance of adjustment of the ultrasonic probe may be sent to an ultrasonic probe controller, so that the ultrasonic probe controller controls the ultrasonic probe to adjust its position according to the angle and the distance.

Exemplarily, after the angle and distance of adjustment of the ultrasonic probe are indicated, the ultrasonic probe may also be adjusted by an operator according to the indicated information.

S105 and S106 above are a feasible implementation for instructing the ultrasonic probe to adjust its position. After the position of the ultrasonic probe is adjusted, S101 and its subsequent steps are executed, the ultrasonic probe is used to acquire ultrasonic echo signals from an updated detected region, and judgment processing is performed to relocate the region of interest of the tissue.

In this embodiment, for the current detected region, when the sizes of the interfering regions in the detected region do not meet the preset condition, the position of the ultrasonic probe may be gradually adjusted to gradually reduce the sizes of interfering regions in the new detected region until the sizes of the interfering regions in the detected region meet the preset condition. At this point, since the interfering regions are small enough, interfering signals corresponding to the interfering regions can be directly removed.

According to the embodiment of the present invention, by gradually adjusting the position of the ultrasonic probe, the sizes of interfering regions in the new detected region are gradually reduced until the sizes of the interfering regions in the detected region meet the preset condition, and at this point, since the interfering regions are small enough, interfering signals corresponding to the interfering regions can be directly removed. Thus, the region of interest can be adaptively located, and the accuracy of locating the region of interest is increased, increasing the accuracy of a result of detection of the region of interest.

Embodiment 3

Figure 3:
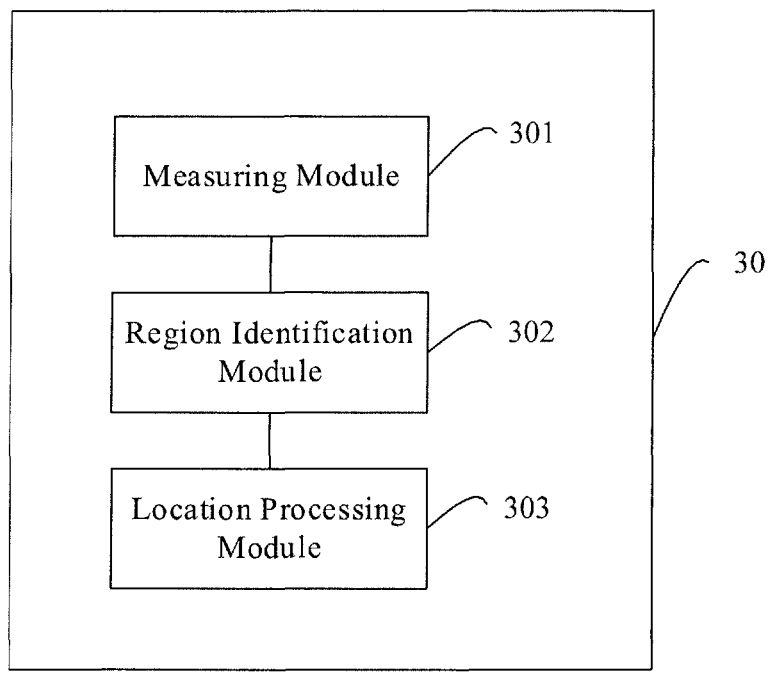
FIG. 3 is a schematic structural diagram of an apparatus for locating a region of interest of a tissue according to Embodiment 3 of the present invention.

FIG. 3 is a schematic structural diagram of an apparatus for locating a region of interest of a tissue according to Embodiment 3 of the present invention. The apparatus for locating a region of interest of a tissue provided by the embodiment of the present invention can execute the processing flow provided by the method for locating a region of interest of a tissue. As shown in FIG. 3, the apparatus 30 for locating a region of interest of a tissue comprises: a measuring module 301, a region identification module 302, and a location processing module 303.

Specifically, the measuring module 301 is configured for acquiring ultrasonic echo signals from a detected region by using an ultrasonic probe.

The region identification module 302 is configured for identifying interfering regions and a region of interest in the detected region according to ultrasonic parameter values of the ultrasonic echo signals.

The location processing module 303 is configured for:

judging whether the sizes of the interfering regions meet a preset condition or not; and if the sizes of the interfering regions meet the preset condition, removing interfering signals corresponding to the interfering regions from the ultrasonic echo signals.

The apparatus provided by the embodiment of the present invention can be specifically used to execute the method embodiment provided by Embodiment 1 described above, and specific functions will not be described here again.

According to the embodiment, ultrasonic echo signals from a detected region are acquired by using an ultrasonic probe; interfering regions and a region of interest in the detected region are identified according to ultrasonic parameter values of the ultrasonic echo signals; whether the sizes of the interfering regions meet a preset condition or not is judged; and if the sizes of the interfering regions meet the preset condition, interfering signals corresponding to the interfering regions are removed from the ultrasonic echo signals. As such, the interfering signals may be removed while the interfering regions are small. Consequently, the region of interest can be adaptively located, and signals with interfering signals removed can be used for signal processing and information extraction related to the region of interest, thereby increasing the accuracy and robustness of signal analysis related to the region of interest and improving the accuracy of a result of detection.

Embodiment 4

On the basis of Embodiment 3 described above, in this embodiment, the location processing module is further configured for:

if the sizes of the interfering regions do not meet the preset condition, instructing the ultrasonic probe to adjust its position to acquire ultrasonic echo signals from an updated detected region, and performing judgment processing.

Optionally, the region identification module is further configured for:

identifying interfering regions and a region of interest in the detected region according to ultrasonic parameter values of the ultrasonic echo signals and characteristic parameter thresholds of the tissue of interest and interfering tissues.

Optionally, the location processing module is further configured for:

determining an angle and distance of adjustment of the ultrasonic probe according to position distributions of the interfering regions and the region of interest in the detected region and an optimal position distribution of the region of interest in the detected region during the detection of the region of interest in an information library; and indicating the angle and distance of adjustment of the ultrasonic probe.

Optionally, the location processing module is further configured for:

judging whether the ratio of the interfering regions to the region of interest is less than an interference ratio threshold or not; if the ratio of the interfering regions to the region of interest is less than the interference ratio threshold, determining that the sizes of the interfering regions meet the preset condition; or if the ratio of the interfering regions to the region of interest is greater than or equal to the interference ratio threshold, determining that the sizes of the interfering regions do not meet the preset condition.

Optionally, the location processing module is further configured for:

judging whether the area of the interfering regions is less than an interfering area threshold or not; if the area occupied by the interfering regions in the detected region is less than the interfering area threshold, determining that the sizes of the interfering regions meet the preset condition; or if the area occupied by the interfering regions in the detected region is greater than or equal to the interfering area threshold, determining that the sizes of the interfering regions do not meet the preset condition.

In this embodiment, the ultrasonic parameter includes one or more of:

scattering peak, scatterer density, scatterer distribution characteristic, reflectance value and reflectance value distribution.

The apparatus provided by the embodiment of the present invention can be specifically used to execute the method embodiment provided by Embodiment 2 described above, and specific functions will not be described here again.

According to the embodiment of the present invention, by gradually adjusting the position of the ultrasonic probe, the sizes of interfering regions in the new detected region are gradually reduced until the sizes of the interfering regions in the detected region meet the preset condition, and at this point, since the interfering regions are small enough, interfering signals corresponding to the interfering regions can be directly removed. Thus, the region of interest can be adaptively located, and the accuracy of locating the region of interest is increased, increasing the accuracy of a result of detection of the region of interest.

Embodiment 5

Figure 4:
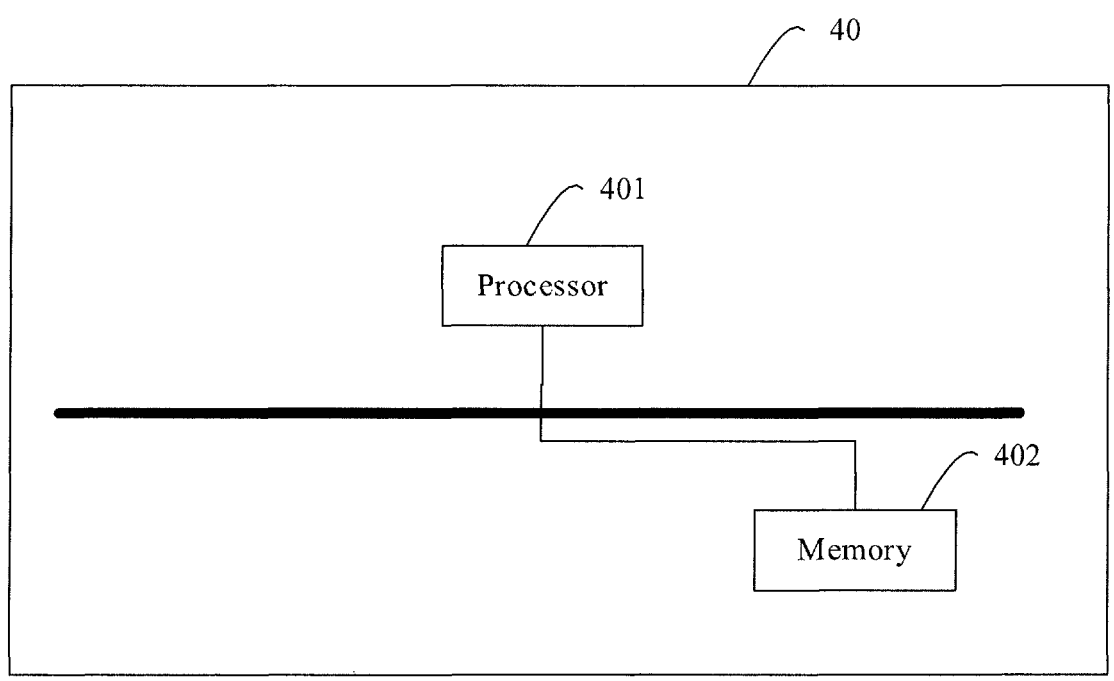
FIG. 4 is a schematic structural diagram of a device for locating a region of interest of a tissue according to Embodiment 5 of the present invention.

FIG. 4 is a schematic structural diagram of a device for locating a region of interest of a tissue according to Embodiment 5 of the present invention. As shown in FIG. 4, the device 40 for locating a region of interest of a tissue comprises: a processor 401, a memory 402, and a computer program stored in the memory 402 and executable by the processor 401, wherein the processor 401 implements the method for locating a region of interest of a tissue provided by any of the method embodiments described above when executing the computer program stored in the memory 402.

According to the embodiment, ultrasonic echo signals from a detected region are acquired by using an ultrasonic probe; interfering regions and a region of interest in the detected region are identified according to ultrasonic parameter values of the ultrasonic echo signals; whether the sizes of the interfering regions meet a preset condition or not is judged; and if the sizes of the interfering regions meet the preset condition, interfering signals corresponding to the interfering regions are removed from the ultrasonic echo signals. As such, the interfering signals may be removed while the interfering regions are small. Consequently, the region of interest can be adaptively located, and signals with interfering signals removed can be used for signal processing and information extraction related to the region of interest, thereby increasing the accuracy and robustness of signal analysis related to the region of interest and improving the accuracy of a result of detection.

In addition, an embodiment of the present invention further provides a computer-readable storage medium having a computer program stored therein, wherein the computer program implements the method for locating a region of interest of a tissue provided by any of the method embodiments described above when executed by a processor.

In the several embodiments provided by the present invention, it should be understood that the disclosed apparatus and method may be implemented in other ways. For example, the above-described apparatus embodiments are merely illustrative, and for example, the division of the units is only a logical function division. Other division methods may be implemented in practice, for example, a plurality of units or components may be combined or integrated into another system, or some features may be omitted, or not executed. In addition, mutual coupling or direct coupling or communication connection shown or discussed may be indirect coupling or communication connection through some interfaces, apparatuses or units, or may be in electrical, mechanical or other forms.

The units described as separate parts may or may not be physically separated, and parts shown as units may or may not be physical units, that is, they may be located at one position or distributed on a plurality of network units. Some or all of the units can be selected according to actual needs to achieve the purpose of the solution of the embodiment.

In addition, functional units in the embodiments of the present invention may be integrated into one processing unit, or each unit may exist alone physically, or two or more units may be integrated into one unit. The aforementioned integrated unit may be implemented in the form of hardware or in the form of hardware plus a functional software unit.

The aforementioned integrated unit implemented in the form of the functional software unit may be stored in a computer-readable storage medium. The aforementioned functional software unit is stored in a storage medium and comprises several instructions for causing a computer device (e.g., a personal computer, a server or a network device) or a processor to execute some steps of the method according to each embodiment of the present invention. The aforementioned storage medium comprises: a USB flash disk, a mobile hard disk, a read-only memory (ROM), a random access memory (RAM), a magnetic disk, an optical disk, or other various media capable of storing program codes.

It is clear to those skilled in the art that for convenience and simplicity of description, the aforementioned division of the functional modules is merely used as an example, and in practical applications, the aforementioned functions may be performed by different functional modules as needed, that is, the internal structure of the apparatus is divided into different functional modules to perform all or part of the above-described functions. For the specific operating process of the apparatus described above, refer to the corresponding processes in the aforementioned method embodiments, which will not be described here again.

Those skilled in the art will easily think of other embodiments of the present invention after considering the specification and practicing the invention disclosed herein. The present invention is intended to cover any variation, use or adaptation of the present invention, which follows the general principle of the present invention and includes the common knowledge or conventional technical means in the art which the present invention has not disclosed. The specification and the embodiments are to be regarded as exemplary only, and the true scope and spirit of the present invention is indicated by the following claims.

It should be understood that the present invention is not limited to the precise structure described above and shown in the drawings, and various modifications and changes can be made without departing from its scope. The scope of the present invention is limited only by the appended claims.

The invention claimed is:

1. A method for locating a region of interest of a tissue based on ultrasonic detection, comprising:
   acquiring, by a processor, ultrasonic echo signals from a detected region by using an ultrasonic probe;
   identifying, by the processor, interfering regions and a region of interest in the detected region according to ultrasonic parameter values of the ultrasonic echo signals, wherein the interfering regions are outside the region of interest and comprise regions corresponding to one or more tissues;
   judging, by the processor, whether the sizes of the interfering regions meet a preset condition or not; and
   if the sizes of the interfering regions meet the preset condition, removing, by the processor, interfering signals which are signals corresponding to the interfering regions from the ultrasonic echo signals,
   wherein after judging whether the sizes of the interfering regions meet a preset condition, or not, the method further comprises:
   if the sizes of the interfering regions do not meet the preset condition, instructing, by the processor, an ultrasonic probe to adjust its position to acquire ultrasonic echo signals from an updated detected region, and performing judgment processing.

2. The method according to claim 1, wherein the tissue comprises a tissue of interest and an interfering tissue, and identifying, by the processor, interfering regions and a region of interest in the detected region according to ultrasonic parameter values of the ultrasonic echo signals comprises:
   identifying, by the processor, interfering regions and a region of interest in the detected region according to ultrasonic parameter values of the ultrasonic echo signals and characteristic parameter thresholds of the tissue of interest and interfering tissues.

3. The method according to claim 1, wherein if the sizes of the interfering regions do not meet the preset condition, instructing, by the processor, an ultrasonic probe to adjust its position comprises:
   determining, by the processor, an angle and distance of adjustment of the ultrasonic probe according to position distributions of the interfering regions and the region of interest in the detected region and an optimal position distribution of the region of interest in the detected region during the detection of the region of interest in an information library; and
   indicating, by the processor, the angle and distance of adjustment of the ultrasonic probe.

4. The method according to claim 1, wherein judging, by the processor, whether the sizes of the interfering regions meet a preset condition or not comprises:
   judging, by the processor, whether a ratio of the interfering regions to the region of interest is less than an interference ratio threshold or not;
   if the ratio of the interfering regions to the region of interest is less than the interference ratio threshold, determining, by the processor, that the sizes of the interfering regions meet the preset condition; and
   if the ratio of the interfering regions to the region of interest is greater than or equal to the interference ratio threshold, determining, by the processor, that the sizes of the interfering regions do not meet the preset condition.

5. The method according to claim 1, wherein judging, by the processor, whether the sizes of the interfering regions meet a preset condition or not comprises:
   judging, by the processor whether the area of the interfering regions is less than an interfering area threshold or not;
   if the area occupied by the interfering regions in the detected region is less than the interfering area threshold, determining, by the processor, that the sizes of the interfering regions meet the preset condition; or
   if the area occupied by the interfering regions in the detected region is greater than or equal to the interfering area threshold, determining, by the processor, that the sizes of the interfering regions do not meet the preset condition.

6. The method according to claim 1, wherein the ultrasonic parameter includes one or more of:
   scattering peak, scatterer density, scatterer distribution characteristic, reflectance value and reflectance value distribution.

7. An apparatus for locating a region of interest of a tissue based on ultrasonic detection, comprising:
   a measuring module, configured for acquiring, by a processor, ultrasonic echo signals from a detected region by using an ultrasonic probe;
   a region identification module, configured for identifying, by the processor, interfering regions and a region of interest in the detected region according to ultrasonic parameter values of the ultrasonic echo signals, wherein the interfering regions are outside the region of interest and comprise regions corresponding to one or more tissues; and a location processing module, configured for:

judging, by the processor, whether the sizes of the interfering regions meet a preset condition or not; and if the sizes of the interfering regions meet the preset condition, removing, by the processor, interfering signals which are signals corresponding to the interfering regions from the ultrasonic echo signals, the location processing module is further configured for:

if the sizes of the interfering regions do not meet the preset condition, instructing, by the processor, an ultrasonic probe to adjust its position to acquire ultrasonic echo signals from an updated detected region, and performing judgment processing.

8. The apparatus according to claim 7, wherein the tissue comprises a tissue of interest and an interfering tissue, and the region identification module is further configured for:

identifying, by the processor, interfering regions and a region of interest in the detected region according to ultrasonic parameter values of the ultrasonic echo signals and characteristic parameter thresholds of the tissue of interest and interfering tissues.

9. The apparatus according to claim 7, wherein the location processing module is further configured for:

determining, by the processor, an angle and distance of adjustment of the ultrasonic probe according to position distributions of the interfering regions and the region of interest in the detected region and an optimal position distribution of the region of interest in the detected region during the detection of the region of interest in an information library; and indicating, by the processor, the angle and distance of adjustment of the ultrasonic probe.

10. A device for locating a region of interest of a tissue based on ultrasonic detection, comprising:

a memory, a processor, and a computer program stored in the memory and executable by the processor, wherein the processor implements the method according to claim 1 when executing the computer program.

11. A computer-readable storage medium having a computer program stored therein, wherein the computer program implements the method according to claim 1 when executed by a processor.

* * * * *